United States Patent
Sale et al.

(10) Patent No.: US 11,739,106 B2
(45) Date of Patent: Aug. 29, 2023

(54) BISPHOSPHITE LIGANDS BASED ON BENZOPINACOL WITH AN OPEN OUTER UNIT

(71) Applicant: EVONIK OPERATIONS GMBH, Essen (DE)

(72) Inventors: Anna Chiara Sale, Recklinghausen (DE); Robert Franke, Marl (DE); Alexander Brächer, Haltern am See (DE); Dirk Fridag, Haltern am See (DE); Ana Markovic, Haltern am See (DE); Peter Kucmierczyk, Herne (DE); Johannes Knossalla, Gahlen (DE); Detlef Selent, Rostock (DE); Armin Börner, Rostock (DE); Kerstin Romeike, Rostock (DE)

(73) Assignee: EVONIK OPERATIONS GMBH, Essen (DE)

(*) Notice: Subject to any disclaimer, the term of this patent is extended or adjusted under 35 U.S.C. 154(b) by 0 days.

(21) Appl. No.: 17/696,038

(22) Filed: Mar. 16, 2022

(65) Prior Publication Data

US 2022/0298183 A1    Sep. 22, 2022

(30) Foreign Application Priority Data

Mar. 18, 2021 (EP) .................................. 21163482

(51) Int. Cl.
*C07F 9/09* (2006.01)
*C07C 45/50* (2006.01)

(52) U.S. Cl.
CPC .................................. *C07F 9/094* (2013.01)

(58) Field of Classification Search
CPC ........ C07F 9/094; C07C 45/505; C07C 45/50
See application file for complete search history.

(56) References Cited

U.S. PATENT DOCUMENTS

| 8,003,816 B2 | 8/2011 | Selent |
| 2002/0103375 A1 | 8/2002 | Selent et al. |
| 2016/0159837 A1 | 6/2016 | Dyballa et al. |

FOREIGN PATENT DOCUMENTS

| DE | 10 2006 058682 A1 | 6/2008 |
| WO | 2008/071508 A1 | 6/2008 |

OTHER PUBLICATIONS

U.S. Appl. No. 17/696,031, filed Mar. 16, 2022, Sale et al.
U.S. Appl. No. 17/696,125, filed Mar. 16, 2022, Sale et al.
European Search Report dated Aug. 20, 2021 for European Patent Application No. 21163482.9 (6 pages in German with Machine Translation).
Singapore Search Report dated May 4, 2023 for Singapore Patent Application No. 10202202645U (2 pages).

*Primary Examiner* — Sikarl A Witherspoon
(74) *Attorney, Agent, or Firm* — Smith, Gambrell & Russell, LLP

(57) ABSTRACT

Bisphosphite ligands based on benzopinacol with an open outer unit, and the use thereof in hydroformylation.

13 Claims, No Drawings

BISPHOSPHITE LIGANDS BASED ON BENZOPINACOL WITH AN OPEN OUTER UNIT

The present invention relates to bisphosphite ligands based on benzopinacol with an open outer unit, and the use thereof in hydroformylation.

WO 2008/071508 A1 describes a process for hydroformylation using bisphosphite ligands. Inter alia, the use of the ligand (D-1) is described.

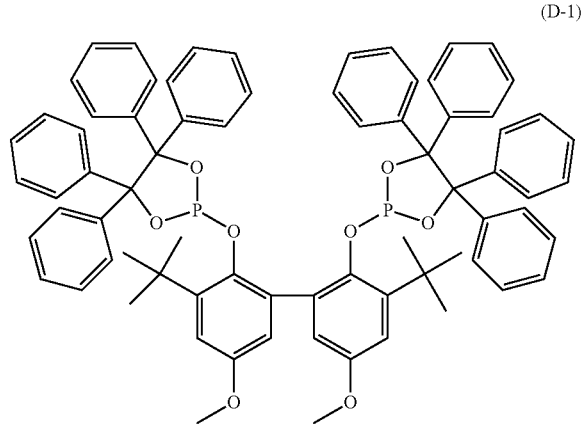 [SMILES: COc1cc(-c2cc(OC)cc(C(C)(C)C)c2OP2OC(c3ccccc3)(c3ccccc3)C(c3ccccc3)(c3ccccc3)O2)c(OP2OC(c3ccccc3)(c3ccccc3)C(c3ccccc3)(c3ccccc3)O2)c(C(C)(C)C)c1]

(D-1)

The technical problem addressed by the present invention is that of providing novel compounds which deliver increased yield in the hydroformylation of olefins compared to the compounds known from the prior art.

This problem is solved by a compound according to Claim 1.

Compound of formula (I):

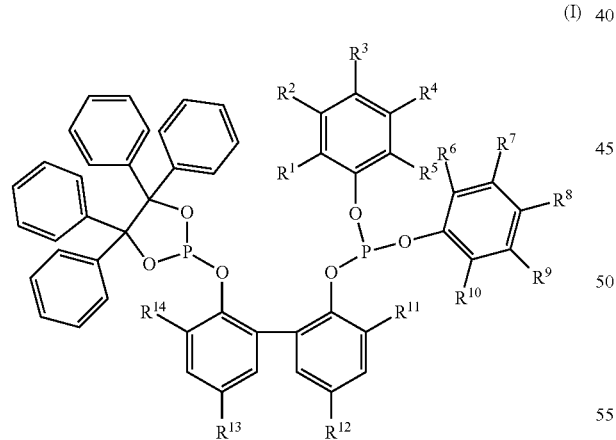

(I)

wherein
$R^1, R^2, R^3, R^4, R^5, R^6, R^7, R^8, R^9, R^{10}, R^{11}, R^{12}, R^{13}, R^{14}$ are each independently selected from: —H, —($C_1$-$C_{12}$)-alkyl, —O—($C_1$-$C_{12}$)-alkyl, —($C_4$-$C_{12}$)-aryl, and the radicals $R^1, R^2, R^3, R^4, R^5$, and also the radicals $R^6, R^7, R^8, R^9, R^{10}$, may form fused systems with one another.

The radicals $R^1, R^2, R^3, R^4, R^5$ may therefore be connected to one another via a ring or a plurality of rings and thus form a new aromatic system. The same correspondingly applies to the radicals $R^6, R^7, R^8, R^9, R^{10}$. In contrast, for example, no fused systems may be formed between the radicals $R^5$ and $R^6$. The radicals $R^5$ and $R^6$ are not located on the same phenyl radical.

The expressions —($C_1$-$C_{12}$)-alkyl and —O—($C_1$-$C_{12}$)-alkyl encompass straight-chain and branched alkyl groups having 1 to 12 carbon atoms. These are preferably —($C_1$-$C_8$)-alkyl groups or —O—($C_1$-$C_8$)-alkyl groups, particularly preferably —($C_1$-$C_4$)-alkyl groups or —O—($C_1$-$C_4$)-alkyl groups.

In one embodiment, $R^{11}$ and $R^{14}$ are —($C_1$-$C_{12}$)-alkyl.

In one embodiment, $R^{11}$ and $R^{14}$ are -$^{tert}$Bu.

In one embodiment, $R^{12}, R^{13}$ are selected from: —($C_1$-$C_{12}$)-alkyl, —O—($C_1$-$C_{12}$)-alkyl.

In one embodiment, $R^{12}$ and $R^{13}$ are —$OCH_3$ or -$^{tert}$Bu.

In one embodiment, $R^{12}$ and $R^{13}$ are —$OCH_3$.

In one embodiment, $R^1, R^2, R^3, R^4, R^5, R^6, R^7, R^8, R^9, R^{10}$ are selected from —H, —($C_1$-$C_{12}$)-alkyl, —($C_4$-$C_{12}$)-aryl.

In one embodiment, $R^1, R^2, R^3, R^4, R^5, R^6, R^7, R^8, R^9, R^{10}$ are selected from —H, -$^{tert}$Bu, —($C_4$-$C_6$)-aryl.

In one embodiment, the compound has one of the structures (1) to (3):

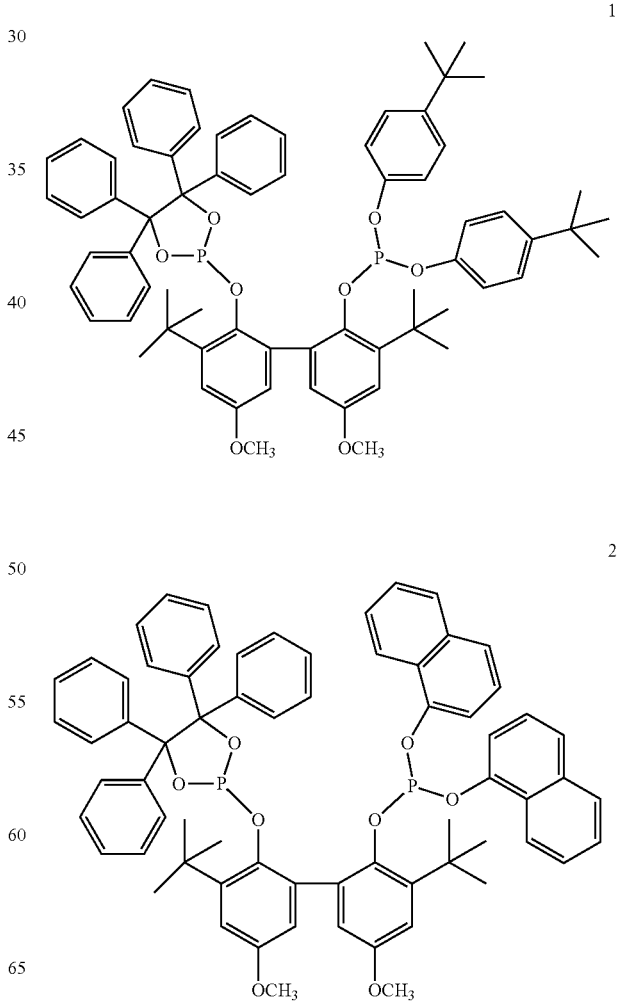

-continued

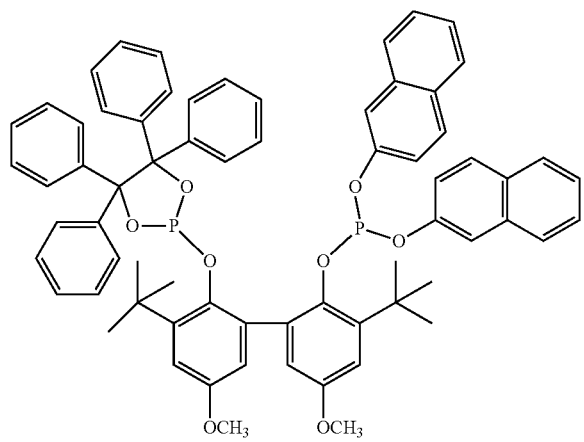

3

In addition to the compound per se, a process in which the compound is used is also claimed.

Process comprising the process steps of:

a) initially charging an ethylenically unsaturated compound;

b) adding a compound as described above and a substance comprising Rh;

c) feeding in $H_2$ and CO, e) heating the reaction mixture from a) to c), with conversion of the ethylenically unsaturated compound to an aldehyde.

In this process, process steps a), b) and c) can be effected in any desired sequence. Typically, however, CO is added after the co-reactants have been initially charged in steps a) and b). In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

In one variant of the process, the ethylenically unsaturated compound does not comprise any further functional groups apart from carbon-carbon double bonds.

In one variant of the process, the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

In one variant of the process, the substance comprising Rh is selected from: Rh(acac)(CO)$_2$, [(acac)Rh(COD)] (Umicore, acac=acetylacetonate anion; COD=1,5-cyclooctadiene), Rh$_4$CO$_{12}$.

In one variant of the process, CO is fed in in process step c) at a pressure in the range from 1 to 6 MPa (10 to 60 bar).

In one variant of the process, the reaction mixture is heated in process step d) to a temperature in the range from 80° C. to 160° C.

The invention shall be elucidated in more detail hereinbelow with reference to working examples.

Synthesis of bis(4-(tert-butyl)phenyl) (3,3-di-tert-butyl-5,5'-dimethoxy-2'-(4,4,5-tetraphenyl-1,3,2-dioxaphospholan-2-yl)oxy)-[1,1'-biphenyl]-2-yl) phosphite (1)

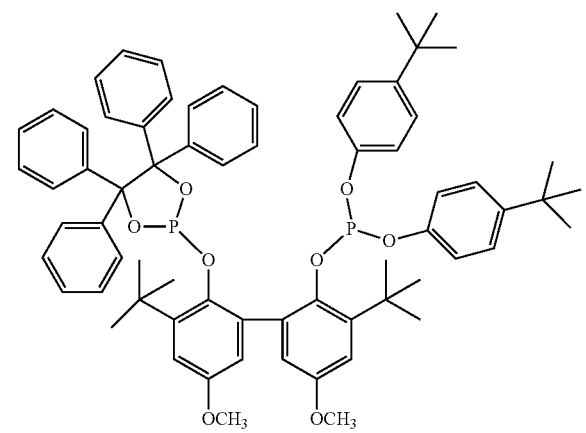

1

To a solution of 2-((3,3'-di-tert-butyl-2'-((dichlorophosphanyl)oxy)-5,5'-dimethoxy-[1,1'-biphenyl]-2-yl)oxy)-4,4,5,5-tetraphenyl-1,3,2-dioxaphospholane (0.7254 g; 0.8496 mmol) in 10 ml of toluene is added dropwise, at room temperature, a mixture of 4-tert-butylphenol (0.2808 g; 1.8691 mmol) and triethylamine (2.39 ml) in 8 ml of toluene. The mixture is stirred overnight and filtered, and the filtrate is concentrated to dryness under reduced pressure. The solid obtained is dried at 60° C./0.1 mbar for 2 h. Yield: 0.869 g (0.8036 mmol, 94%).

Elemental analysis (calc. for $C_{66}H_{74}O_8P_2$=1081.273 g/mol): C=75.43 (75.53): H=7.06 (6.90); P=5.79 (5.73).

ESI-TOF HRMS: m/z=1103.4775; [M$^+$+Na], calc. m/z=1103.4756.

$^{31}$P NMR (CD$_2$Cl$_2$): δ 132.2 (d, J$_{PP}$=49 Hz); 145.3 (d, J$_{PP}$=49 Hz).

$^1$H NMR (CD$_2$Cl$_2$): δ 1.15 (s, 9H); 1.33 (s, 9H); 1.35 (s, 9H); 1.53 (s, 9H); 3.55 (s, 3H); 3.76 (s, 3H); 6.71-7.43 (m, 32H) ppm.

Synthesis of 3,3'-di-tert-butyl-5,5'-dimethoxy-2'-((4,4,5,5-tetraphenyl-1,3,2-dioxapholan-2-yl)oxy)-[1,1'-biphenyl]-2-yl di(naphthalen-1-yl) phosphite (2):

Synthesis of 3,3'-di-tert-butyl-5,5'-dimethoxy-2'-((4,4,5,5-tetraphenyl-1,3,2-dioxapholan-2-yl)oxy)-[1,1'-biphenyl]-2-yl di(naphthalen-2-yl) phosphite (3):

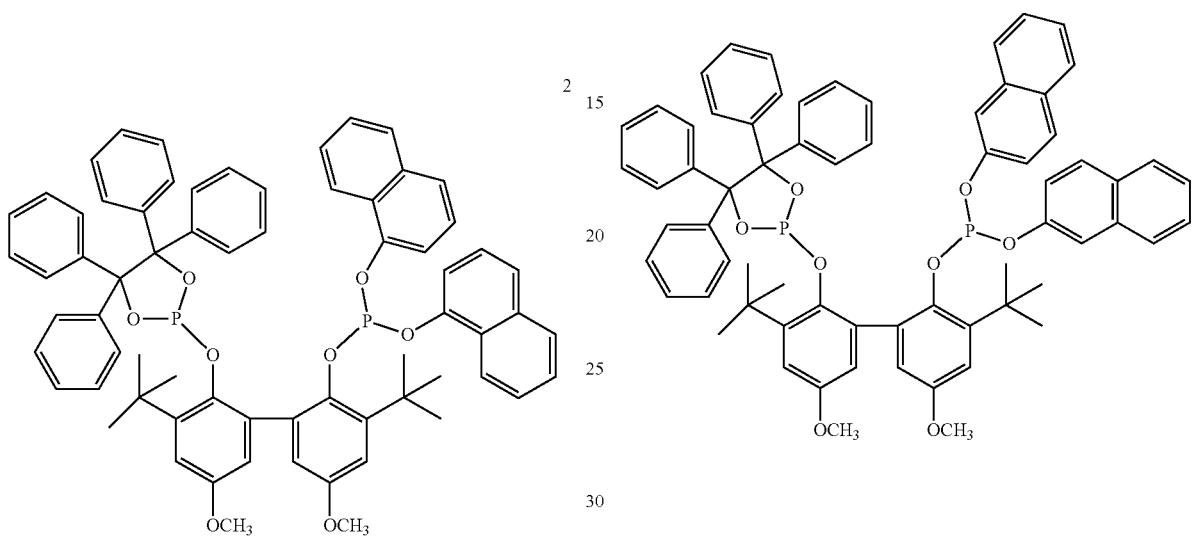

To a solution of 2-((3,3'-di-tert-butyl-2'-((dichlorophosphanyl)oxy)-5,5'-dimethoxy-[1,1'-biphenyl]-2-yl)oxy)-4,4,5,5-tetraphenyl-1,3,2-dioxaphospholane (0.5622 g; 0.6585 mmol) in 8 ml of toluene is added dropwise, at room temperature, a mixture of 1-naphthol (0.2088 g; 1.4487 mmol) and triethylamine (1.85 ml) in 6 ml of toluene. The mixture is stirred overnight and filtered, and the filtrate is concentrated to dryness under reduced pressure. The solid obtained is dried at 60° C./0.1 mbar for 2 h and then taken up in 6 ml of hot acetonitrile. The solid obtained after storing the solution at −29° C. is separated off, washed with a little cold acetonitrile and dried. Yield: 0.480 g (0.449 mmol, 68%).

Elemental analysis (calc. for $C_{68}H_{62}O_8P_2$=1069.178 g/mol): C=76.36 (76.39); H=5.95 (5.85); P=5.67 (5.79).

ESI-TOF HRMS: m/z=1091.3801; [M$^+$+Na], calc. m/z=1091.3817.

$^{31}$P NMR (CD$_2$Cl$_2$): δ 135.5 (d, $J_{PP}$=30 Hz); 146.2 (d, $J_{PP}$=30 Hz) ppm.

$^1$H NMR (CD$_2$Cl$_2$): δ 1.14 (s, 9H); 1.63 (s, 9H); 2.94 (s, 3H); 3.87 (s, 3H); 6.33 (d, $^4J_{HH}$=3.1 Hz; 1H); 6.74 (d, $^4J_{HH}$=3.1 Hz; 1H); 6.89-7.84 (m, 35H); 8.12 (m, 1H) ppm.

To a solution of 2-((3,3'-di-tert-butyl-2'-((dichlorophosphanyl)oxy)-5,5'-dimethoxy-[1,1'-biphenyl]-2-yl)oxy)-4,4,5,5-tetraphenyl-1,3,2-dioxaphospholane (0.5971 g; 0.6993 mmol) in 8 ml of toluene is added dropwise, at room temperature, a mixture of 2-naphthol (0.2218 g; 1.5386 mmol) and triethylamine (1.96 ml) in 6 ml of toluene. The mixture is stirred overnight and filtered, and the filtrate is concentrated to dryness under reduced pressure. The solid obtained is dried at 60° C./0.1 mbar for 2 h and then taken up in 6.5 ml of hot acetonitrile. The solid obtained after storing the solution at −29° C. is separated off, washed with a little cold acetonitrile and dried. Yield: 0.470 g (0.439 mmol, 63%).

Elemental analysis (calc. for $C_{68}H_{62}O_8P_2$=1069.178 g/mol): C=76.18 (76.39); H=5.88 (5.85); P=5.74 (5.79).

ESI-TOF HRMS: m/z=1091.3811; [M$^+$+Na], calc. m/z=1091.3817.

$^{31}$P NMR (CD$_2$Cl$_2$): δ 131.8 (d, $J_{PP}$=56 Hz); 145.0 (d, $J_{PP}$=56 Hz) ppm.

$^1$H NMR (CD$_2$CO$_2$): δ 1.15 (s, 9H); 1.58 (s, 9H); 3.48 (s, 3H); 3.77 (s, 3H); 6.78 (m, 1H); 6.83 (m, 1H); 6.86 (m, 1H); 6.93-7.03 (m, 8H); 7.07-7.23 (m, 11); 7.35-7.52 (m, 10H); 7.66 (m, 1H): 7.72-7.85 (m, 5H) ppm.

Catalysis Experiments

The hydroformylation was conducted in a 200 ml autoclave from Premex Reactor AG, Lengau, Switzerland, equipped with pressure-retaining valve, gas flow meter, sparging stirrer and pressure pipette. To minimize the influence of moisture and oxygen, the toluene used as solvent was purified in a Pure Solv. MD-7 System and stored under argon. The olefin cis/trans-2-pentene used as substrate (Aldrich) was heated at reflux over sodium and distilled under argon. Toluene solutions of the catalyst precursor and of the ligand were mixed in the autoclave under an argon atmosphere. [(acac)Rh(COD)] (Umicore, acac=acetylacetonate anion; COD=1,5-cyclooctadiene) was used as catalyst precursor. The autoclave was heated with stirring (1500 rpm) at 12 bar for a final pressure of 20 bar. After reaching the reaction temperature, the olefin was injected into the autoclave by way of a positive pressure established in the pressure pipette. The reaction was conducted at a constant pressure (closed-loop pressure controller from Bronkhorst, the Netherlands) over 4 h. At the end of the reaction time, the autoclave was cooled to room temperature, depressurized while stirring and purged with argon. 1 ml of each reaction mixture was removed immediately after the stirrer had been switched off, diluted with 10 ml of pentane and analysed by gas chromatography: HP 5890 Series II plus, PONA, 50 m×0.2 mm×0.5 μm.

The reaction was conducted using compounds (1) to (3) according to the invention and using the comparative ligand (D-1).

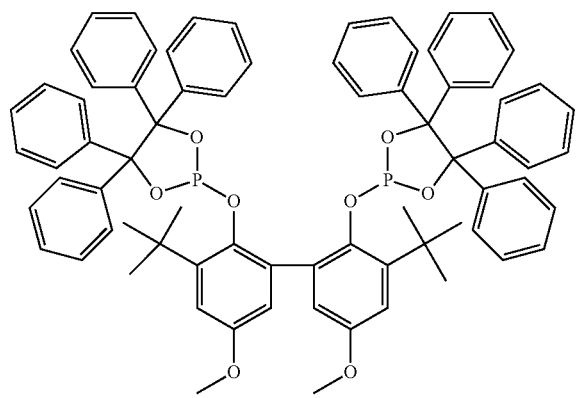

(D-1)

Reaction Conditions:

Olefin: 2-pentene, solvent: toluene, proportion by mass of rhodium: 100 ppm, p: 20 bar, T: 120° C., t: 4 h, Rh:ligand ratio=1:2.

The results are compiled in the following table:

| Ligand | Yield of aldehyde [%] |
|---|---|
| 1* | 46 |
| 2* | 45 |
| 3* | 50 |
| D-1 | 14 |

*compound according to the invention

As the experimental results show, the problem is solved by the compounds according to the invention.

The invention claimed is:

1. A compound of formula (I):

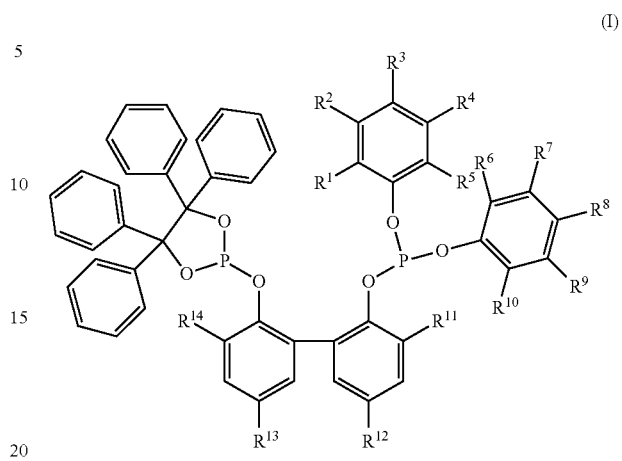

(I)

wherein
$R^1, R^2, R^3, R^4, R^5, R^6, R^7, R^8, R^9, R^{10}, R^{11}, R^{12}, R^{13}, R^{14}$ are each independently selected from: —H, —($C_1$-$C_{12}$)-alkyl, —O—($C_1$-$C_{12}$)-alkyl or —($C_4$-$C_{12}$)-aryl, and the radicals $R^1, R^2, R^3, R^4$, and also the radicals $R^6, R^7, R^8, R^9, R^{10}$, may form fused systems with one another.

2. The compound according to claim 1, wherein $R^{11}$ and $R^{14}$ are —($C_1$-$C_{12}$)-alkyl.

3. The compound according to claim 1, wherein $R^{11}$ and $R^{14}$ are -$^{tert}$Bu.

4. The compound according to claim 1, wherein $R^2, R^{13}$ are selected from: —($C_1$-$C_{12}$)-alkyl or, —O—($C_1$-$C_{12}$)-alkyl.

5. The compound according to claim 1, wherein $R^{12}$ and $R^{13}$ are —$OCH_3$ or -$^{tert}$Bu.

6. The compound according to claim 1, wherein $R^1, R^2, R^3, R^4, R^5, R^6, R^7, R^8, R^9, R^{10}$ are selected from —H, —($C_1$-$C_{12}$)-alkyl or —($C_4$-$C_{12}$)-aryl.

7. The compound according to claim 1, wherein $R^1, R^2, R^3, R^4, R^5, R^6, R^7, R^8, R^9, R^{10}$ are selected from —H, -$^{tert}$Bu, —($C_4$-$C_6$)-aryl.

8. The compound according to claim 1, wherein the compound has one of the structures (1) to (3):

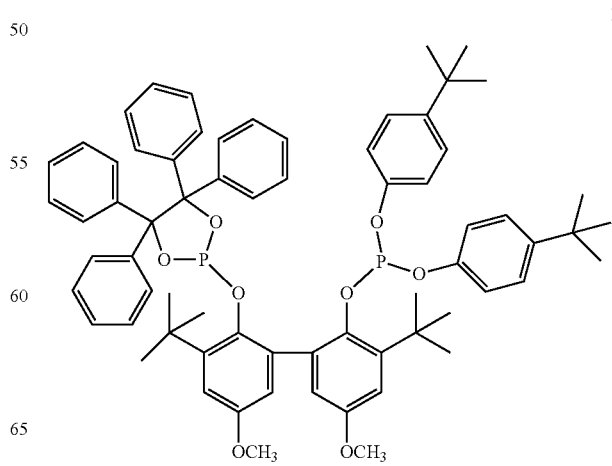

1

-continued

2

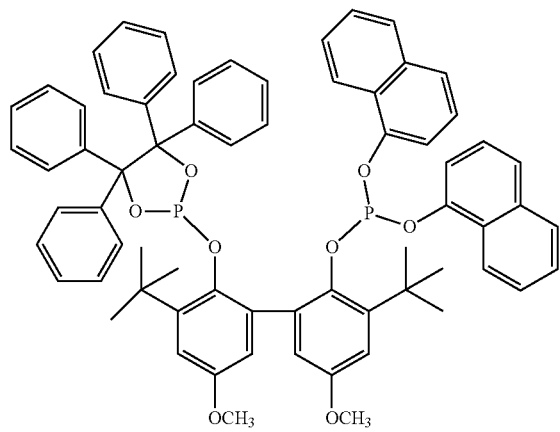

3

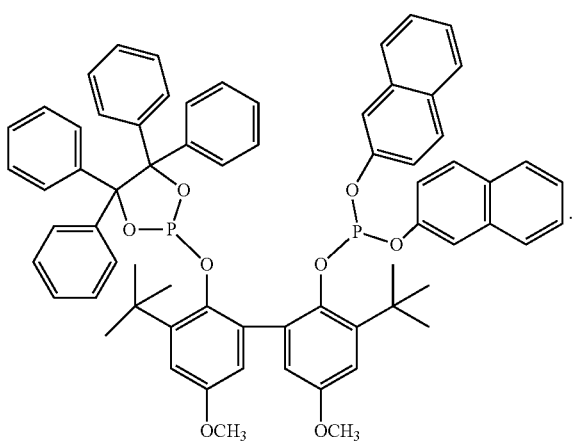

9. A process comprising the process steps of:
a) initially charging an ethylenically unsaturated compound;
b) adding a compound according to claim 1;
and a substance comprising Rh;
c) feeding in $H_2$ and CO, and
d) heating the reaction mixture from a) to c), with conversion of the olefin to an aldehyde.

10. The process according to claim 9,
wherein the ethylenically unsaturated compound in process step a) is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

11. The process according to claim 9,
wherein the substance comprising Rh is selected from: $Rh(acac)(CO)_2$, [(acac)Rh(COD)] (Umicore, acac=acetylacetonate anion; COD=1,5-cyclooctadiene), $Rh_4CO_{12}$.

12. The process according to claim 9,
wherein CO is fed in in process step c) at a pressure in the range from 1 to 6 MPa (10 to 60 bar).

13. The process according to claim 9,
wherein the reaction mixture is heated in process step d) to a temperature in the range from 80° C. to 160° C.

* * * * *